United States Patent
Lynde et al.

(10) Patent No.: US 10,791,964 B2
(45) Date of Patent: Oct. 6, 2020

(54) HEART RATE MONITOR

(71) Applicant: INNOVAURA CORPORATION, Edmonds, WA (US)

(72) Inventors: C. Macgill Lynde, Bellevue, WA (US); Alan B. Corwin, Bremerton, WA (US); Ronald J. Schoenberg, Burien, WA (US); Keith Mullins, Kent, WA (US); David B. Goodson, Bellevue, WA (US); Christopher A. Wiklof, Everett, WA (US)

(73) Assignee: INNOVAURA CORPORATION, Edmonds, WA (US)

( * ) Notice: Subject to any disclaimer, the term of this patent is extended or adjusted under 35 U.S.C. 154(b) by 267 days.

(21) Appl. No.: 15/591,918

(22) Filed: May 10, 2017

(65) Prior Publication Data
US 2017/0311849 A1    Nov. 2, 2017

Related U.S. Application Data

(63) Continuation of application No. PCT/US2015/060209, filed on Nov. 11, 2015.
(Continued)

(51) Int. Cl.
*A61B 5/11* (2006.01)
*A61B 5/00* (2006.01)
(Continued)

(52) U.S. Cl.
CPC .......... *A61B 5/1102* (2013.01); *A61B 5/0004* (2013.01); *A61B 5/024* (2013.01); *A61B 5/0255* (2013.01); *A61B 5/02438* (2013.01); *A61B 5/04005* (2013.01); *A61B 5/04007* (2013.01); *A61B 5/05* (2013.01); *A61B 5/1126* (2013.01); *A61B 5/6824* (2013.01); *A61B 5/725* (2013.01);
(Continued)

(58) Field of Classification Search
CPC . A61B 5/1102; A61B 5/7257; A61B 5/02438; A61B 5/0255; A61B 5/04007; A61B 5/1126; A61B 5/742; A61B 5/7278; A61B 5/0004; A61B 5/725; A61B 5/7221; A61B 5/6824; A61B 2560/0214; A61B 2562/0219; A61B 2562/0223; A61B 2562/164; A61B 2562/18
USPC .................................................. 600/407, 409
See application file for complete search history.

(56) References Cited

U.S. PATENT DOCUMENTS 4,853,630 A * 8/1989 Houston ................. G01B 7/003
                                                      324/207.13
5,069,221 A * 12/1991 Smith ................. A61B 5/02455
                                                       324/207.2
(Continued)

OTHER PUBLICATIONS

PCT International Search Report and Written Opinion of PCT Application No. PCT/US2015/060209 dated Feb. 22, 2016.

*Primary Examiner* — Oommen Jacob
(74) *Attorney, Agent, or Firm* — Christopher A. Wiklof; Nicholas S. Bromer; Launchpad IP, Inc.

(57) ABSTRACT

A heart rate monitor includes a magnet supported to move responsive to an arterial pulse and a magnetometer configured to detect changes in a magnetic field produced by the magnet. The magnet can include a plurality of ferromagnetic particles disposed in or on a flexible substrate configured to be held adjacent to human skin subject to arterial palpation and a magnetic sensor configured to sense movement of the ferromagnetic particles.

38 Claims, 11 Drawing Sheets

Related U.S. Application Data

(60) Provisional application No. 62/078,012, filed on Nov. 11, 2014, provisional application No. 62/078,387, filed on Nov. 11, 2014.

(51) Int. Cl.
*A61B 5/04* (2006.01)
*A61B 5/05* (2006.01)
*A61B 5/024* (2006.01)
*A61B 5/0255* (2006.01)

(52) U.S. Cl.
CPC .......... *A61B 5/7221* (2013.01); *A61B 5/7257* (2013.01); *A61B 5/7278* (2013.01); *A61B 5/742* (2013.01); *A61B 2560/0214* (2013.01); *A61B 2562/0219* (2013.01); *A61B 2562/0223* (2013.01); *A61B 2562/164* (2013.01); *A61B 2562/18* (2013.01)

(56) References Cited

U.S. PATENT DOCUMENTS

| | | | | |
|---|---|---|---|---|
| 7,391,210 | B2* | 6/2008 | Zhang | G01R 33/04 324/244 |
| 8,394,067 | B2* | 3/2013 | Bracken | A61M 25/02 604/180 |
| 8,923,941 | B2* | 12/2014 | LeBoeuf | A61B 5/00 600/310 |
| 9,770,600 | B1* | 9/2017 | Demas | A61N 2/002 |
| 2003/0144705 | A1* | 7/2003 | Funke | A61N 1/37 607/27 |
| 2003/0212335 | A1* | 11/2003 | Huang | A61B 5/021 600/500 |
| 2004/0061620 | A1* | 4/2004 | Devine | G08B 13/1409 340/689 |
| 2005/0274454 | A1* | 12/2005 | Extrand | C09J 5/00 156/272.4 |
| 2006/0122484 | A1* | 6/2006 | Itozaki | G01R 33/441 600/409 |
| 2006/0206031 | A1 | 9/2006 | Hasegawa | |
| 2006/0229809 | A1 | 10/2006 | Chen | |
| 2007/0179386 | A1 | 8/2007 | Michard et al. | |
| 2008/0047154 | A1* | 2/2008 | Steinich | G01C 9/06 33/366.17 |
| 2011/0054270 | A1 | 3/2011 | Derchak | |
| 2012/0197093 | A1* | 8/2012 | LeBoeuf | G06F 19/00 600/301 |
| 2013/0099735 | A1* | 4/2013 | Partovi | H01F 7/0252 320/108 |
| 2013/0165766 | A1* | 6/2013 | Nishikawa | A61B 5/04007 600/409 |
| 2014/0228649 | A1* | 8/2014 | Rayner | A61B 5/1118 600/301 |
| 2014/0243617 | A1* | 8/2014 | LeBoeuf | A61B 5/0059 600/301 |
| 2014/0275854 | A1* | 9/2014 | Venkatraman | A61B 5/721 600/301 |
| 2014/0288391 | A1 | 9/2014 | Hong et al. | |
| 2015/0057511 | A1* | 2/2015 | Basu | A61B 5/02433 600/323 |
| 2015/0105630 | A1* | 4/2015 | Kummerl | A61B 5/02438 600/301 |
| 2015/0182160 | A1* | 7/2015 | Kim | A61B 5/0488 600/301 |
| 2016/0007925 | A1* | 1/2016 | Mirov | A61B 5/02427 356/400 |
| 2016/0213560 | A1* | 7/2016 | Sturdivant | A61H 31/006 |
| 2016/0262687 | A1* | 9/2016 | Vaidyanathan | A61B 5/7264 |
| 2016/0327915 | A1* | 11/2016 | Katzer | G04B 19/04 |
| 2017/0311849 | A1* | 11/2017 | Lynde | A61B 5/742 |

* cited by examiner

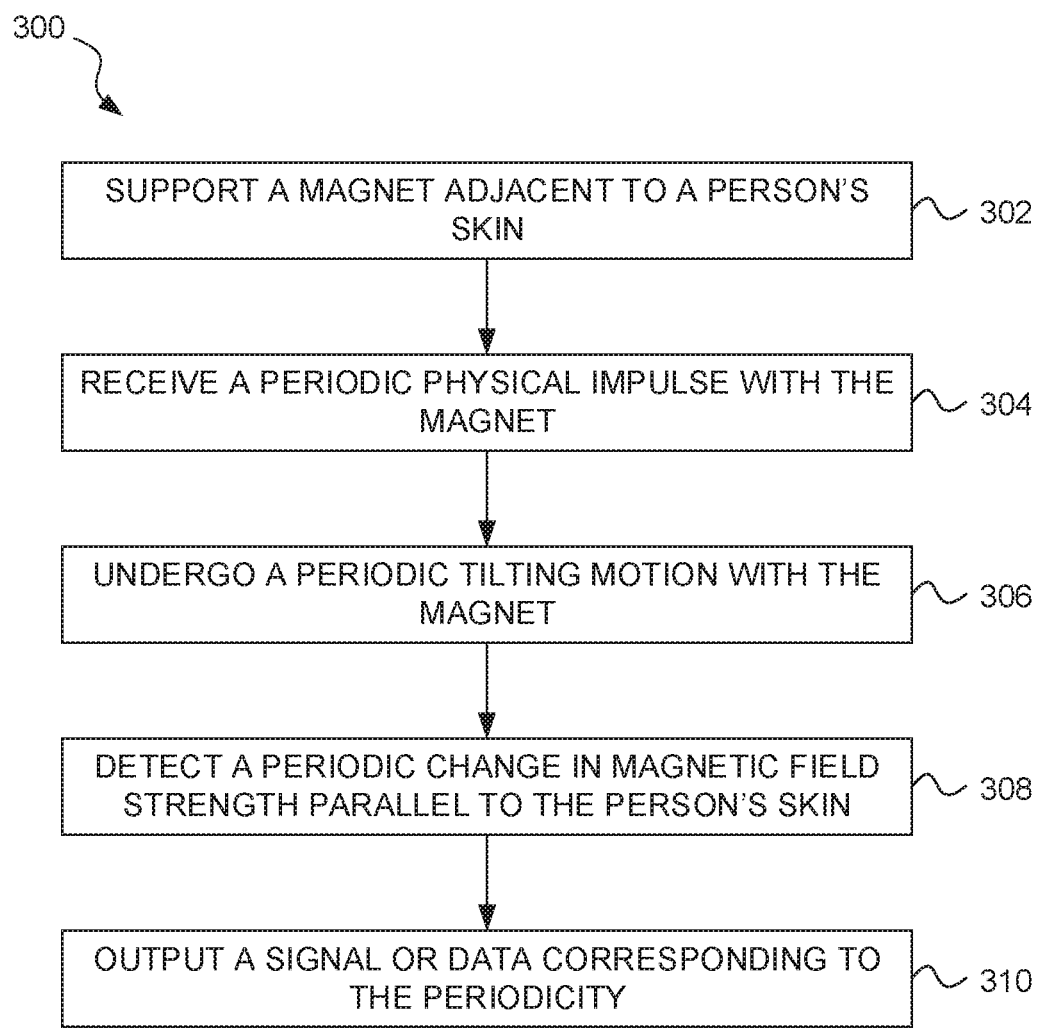

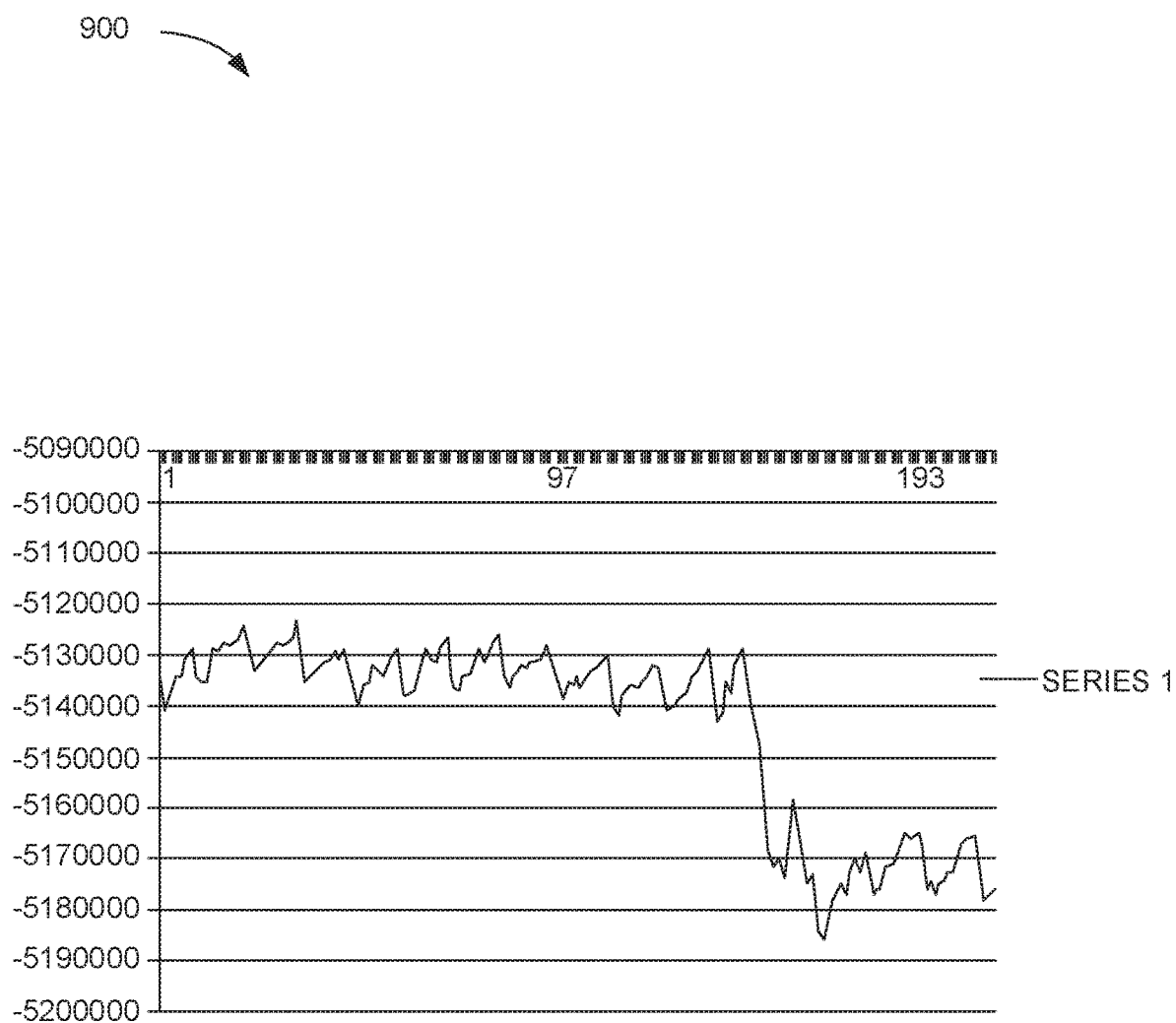

HEART RATE MONITOR

CROSS-REFERENCE TO RELATED APPLICATIONS

The present application is a U.S. Continuation Application which claims priority benefit under 35 U.S.C. § 120 of co-pending International Patent Application No. PCT/US2015/060209, entitled "HEART RATE MONITOR," filed Nov. 11, 2015, co-pending at the time of filing; which application claims priority benefit from U.S. Provisional Patent Application No. 62/078,012, entitled "HEART RATE MONITOR WITH MOTION-SENSING," filed Nov. 11, 2014, and from U.S. Provisional Patent Application No. 62/078,387, entitled "MAGNETIC TRANSDUCER AND SYSTEM FOR DETECTING A PULSE," filed Nov. 11, 2014; each of which, to the extent not inconsistent with the disclosure herein, is incorporated herein by reference.

BACKGROUND

Heart rate monitors are used by fitness-tracking applications to assess user fitness and activity level, and to provide real time feedback to the user regarding exercise intensity. Heretofore, many consumer-level heart rate monitors for use with fitness-tracking applications have required separate mounting of the heart rate monitor near the user's sternum (which can be uncomfortable) and/or have used optical pulse measurement apparatuses characterized by relatively high power consumption and by inaccuracies associated with motion of the user What is needed is a pulse or heart rate monitor that is convenient and comfortable, which requires lower power to operate, and is accurate during exercise.

SUMMARY

According to an embodiment, a heart rate monitor includes at least one magnet disposed adjacent to a user's artery subject to pulse movement, the magnet being subject to movement responsive to the arterial pulse movement. A magnetometer is configured to be exposed to a magnetic field produced by the at least one magnet and to measure variations in the magnetic field corresponding to the movement of the magnet responsive to the arterial pulse movement. A sensing circuit is operatively coupled to the magnetometer and configured to infer a heart rate corresponding to the sensed variations in the magnetic field.

According to an embodiment, a heart rate monitor includes a flexible membrane configured to be held adjacent to a user's skin at a location corresponding to an artery subject to pulse movement and at least one magnet having a magnetic axis, the magnet being disposed on the flexible membrane and being configured to physically tilt responsive to the pulse movement, whereby the magnetic axis tilts. A magnetometer is configured to measure a magnetic field produced by the at least one magnet, the magnetometer having a magnetic field measurement axis along which the magnetic axis tilt causes a change in measured magnetic field strength.

According to another embodiment, a heart rate monitor includes a flexible membrane configured to be held adjacent to a user's skin at a location corresponding to an artery subject to pulse movement, at least one magnet disposed on the flexible membrane and configured to move responsive to the pulse movement, and a magnetometer configured to measure variations in a magnetic field from the at least one magnet responsive to the pulse movement. A motion sensor can be configured to detect movement of the human. A microcontroller operatively coupled to the magnetometer and the motion sensor can include a non-transitory computer-readable medium carrying microcontroller instructions configured to cause the microcontroller to receive data or a signal from the magnetometer, receive detected movement information from the motion sensor, filter the data or signal from the first magnetometer responsive to the detected movement, and output heart rate data corresponding to the filtered data or signal from the first magnetometer.

According to embodiments, the motion sensor can also provide user motion data to fitness and health tracking applications, devices, and/or systems. In a particular embodiment, a sensor device outputs motion data and heart rate data to a fitness or health tracking application. The fitness or health tracking application is embodied as a non-transitory computer readable medium carrying computer instructions that cause the application to correlate a sequence of motion data to a corresponding sequence of heart rate data. The application can perform logical operations, for example using Bayesian logic, on the correlated data to determine a probability of a user having a fitness corresponding to any of a plurality of levels; and display the most probable fitness level to the user.

According to an embodiment, a method for detecting a heart rate includes supporting a magnet adjacent to the skin of a person, receiving a periodic physical impulse with the magnet responsive to arterial movement during systole and diastole, and undergoing a periodic tilting motion of the magnet responsive to the periodic physical impulse corresponding to systole and diastole. A magnetometer detects a periodic change in the strength of the magnetic field produced by the magnet along an axis parallel to the person's skin and outputs a magnetometer signal or magnetometer data corresponding to a periodicity of the detected periodic change in the strength of the magnetic field. The output signal or data includes a component corresponding to a heart rate of the person.

According to an embodiment, a method for tracking the heart rate of a person includes flexibly supporting a magnet adjacent to a pulse detection location of a person, undergoing, with the magnet, movement responsive to pulse movement of the person, and operating a magnetometer to detect periodic changes in magnetic field strength from the magnet, the periodic changes in magnetic field strength corresponding to the movement of the magnet and the pulse movement of the person. A microcontroller receives the magnetometer data including the periodic changes in magnetic field strength from the magnet and transforms the magnetometer data to produce frequency data. The microcontroller receives motion data corresponding to movement of the person from a motion detector. The microcontroller uses the motion data to filter the frequency data to select a frequency most likely to correspond to a pulse rate of the person.

According to an embodiment, a pulse sensor includes a flexible substrate configured for support against a human skin surface, a plurality of aligned magnetic dipoles supported by the flexible substrate, a magnetic sensor configured to detect magnetic fields emitted by the plurality of magnetic dipoles, and an analysis circuit operatively coupled to the magnetic sensor. According to an embodiment, the flexible substrate can include a gel material. The magnetic dipoles can be suspended in the gel. In an embodiment, the magnetic dipoles can be formed from magnetic nano-beads, or alternatively from crushed or otherwise finely divided portions of a poled permanent magnet. In an embodiment, high coercivity magnetic dipoles can be magnetically aligned during manufacture and locked into alignment by cross-linking or otherwise fixing relative alignment of the magnetic dipoles. In another embodiment, high coercivity magnetic dipoles can be held in alignment during use by a magnet configured to pass a magnetic field through the magnetic dipoles.

In another embodiment, the magnetic dipoles can be formed from a low coercivity material. The low coercivity particles can be induced to be aligned magnetic dipoles by a magnet configured to pass a magnetic field through the low coercivity particles.

According to an embodiment, a method for detecting a human pulse includes supporting a flexible substrate carrying aligned magnetic dipoles against a human skin surface subject to motion caused by a human pulse, sensing a time sequence of magnetic field data including a component corresponding to the aligned magnetic dipoles subject to motion caused by the human pulse, and transforming the magnetic field data to heartbeat data corresponding to the sensed human pulse.

According to an embodiment, the method can include mechanically maintaining alignment of the magnetic dipoles. According to another embodiment, the method can include applying a magnetic field to the magnetic dipoles to hold the magnetic dipoles in alignment. According to another embodiment, the magnetic dipoles can be formed as low coercivity particles, and the method can include applying a magnetic field to the low coercivity particles to cause the low coercivity particles to be magnetized in alignment with the magnetic field, thereby becoming aligned magnetic dipoles.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 3 is a flow chart of a method for detecting a heart rate, according to an embodiment.

FIG. 9 is a second plot of heartbeat data from a second experimental run from the experiment described in the Examples section, according to an embodiment.

DETAILED DESCRIPTION

Figure 1:
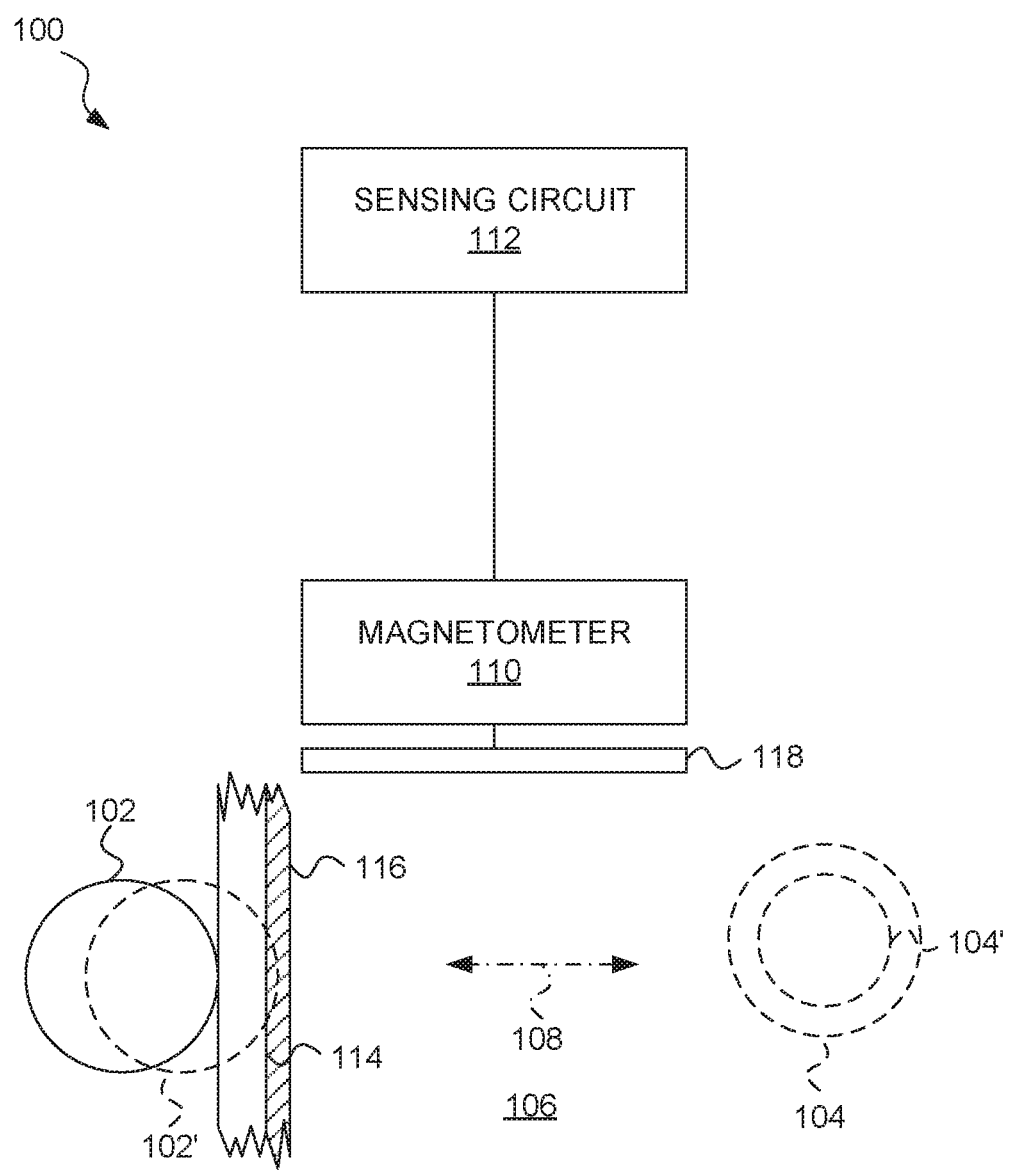
FIG. 1 is a diagram of a heart rate monitor, according to an embodiment.

In the following detailed description, reference is made to the accompanying drawings, which form a part hereof. In the drawings, which are not to scale or to proportion, similar symbols typically identify similar components, unless context dictates otherwise. The illustrative embodiments described in the detailed description, drawings and claims, are not meant to be limiting. Other embodiments may be used and/or other changes may be made without departing from the spirit or scope of the present disclosure.

The terms "heart rate" and "pulse rate" are used interchangeably herein.

FIG. 1 is a diagram of a heart rate monitor 100, according to an embodiment. The heart rate monitor 100 includes at least one magnet 102 disposed adjacent to a user's artery 104 subject to pulse movement, the magnet being subject to movement responsive to the arterial pulse movement. The user's tissue 106 provides compressive and tensile strength 108, and itself conveys motion responsive to the arterial pulsations 104, 104'. The tissue 106 thus conveys motion between locations 102, 102' occupied by the magnet 102. The orientation of the poles of the magnet(s) 102 can be oriented according to various axes as described in respective embodiments below.

A magnetometer 110 is positioned within a magnetic field produced by the at least one magnet 102 and is configured to measure variations in the magnetic field corresponding to the movement of the magnet responsive to the arterial pulse movement. A sensing circuit 112 is operatively coupled to the magnetometer 110 and configured to infer a heart rate corresponding to the sensed variations in the magnetic field. For example, the sensing circuit 112 may be physically coupled to the magnetometer 110.

Alternatively, at least a portion of the sensing circuit can be operatively coupled to the magnetometer 110 via a radio interface. For example, the heart rate monitor 100 can include a first radio communication circuit configured to output data corresponding to a signal from the magnetometer 110 via a radio signal, a second radio communication circuit configured to receive the data from the first radio communication circuit via the radio signal, and a data logging circuit operatively coupled to the second radio circuit. In this arrangement, for example, a portion of the sensing circuit 112 including an analog-to-digital converter can receive analog input from the magnetometer 110, and convert the analog signal to a digital value that is then output via the first and second radio circuits to another portion of the sensing circuit 112.

In an embodiment, a flexible membrane 114 can be configured to be held adjacent to the user's skin at a location corresponding to the artery 104 subject to pulse movement and the at least one magnet 102 can be disposed on the flexible membrane 114. Optionally, a pressure sensitive adhesive coating 116 can be disposed on the flexible membrane 114 to hold the flexible membrane 114 adjacent to the user's skin. In another embodiment, a housing 118 can be configured to support the flexible membrane 114 against the user's skin. In another embodiment, the at least one magnet is subcutaneously embedded within the user's tissue 106 at a location near the artery 104.

Figure 2A:
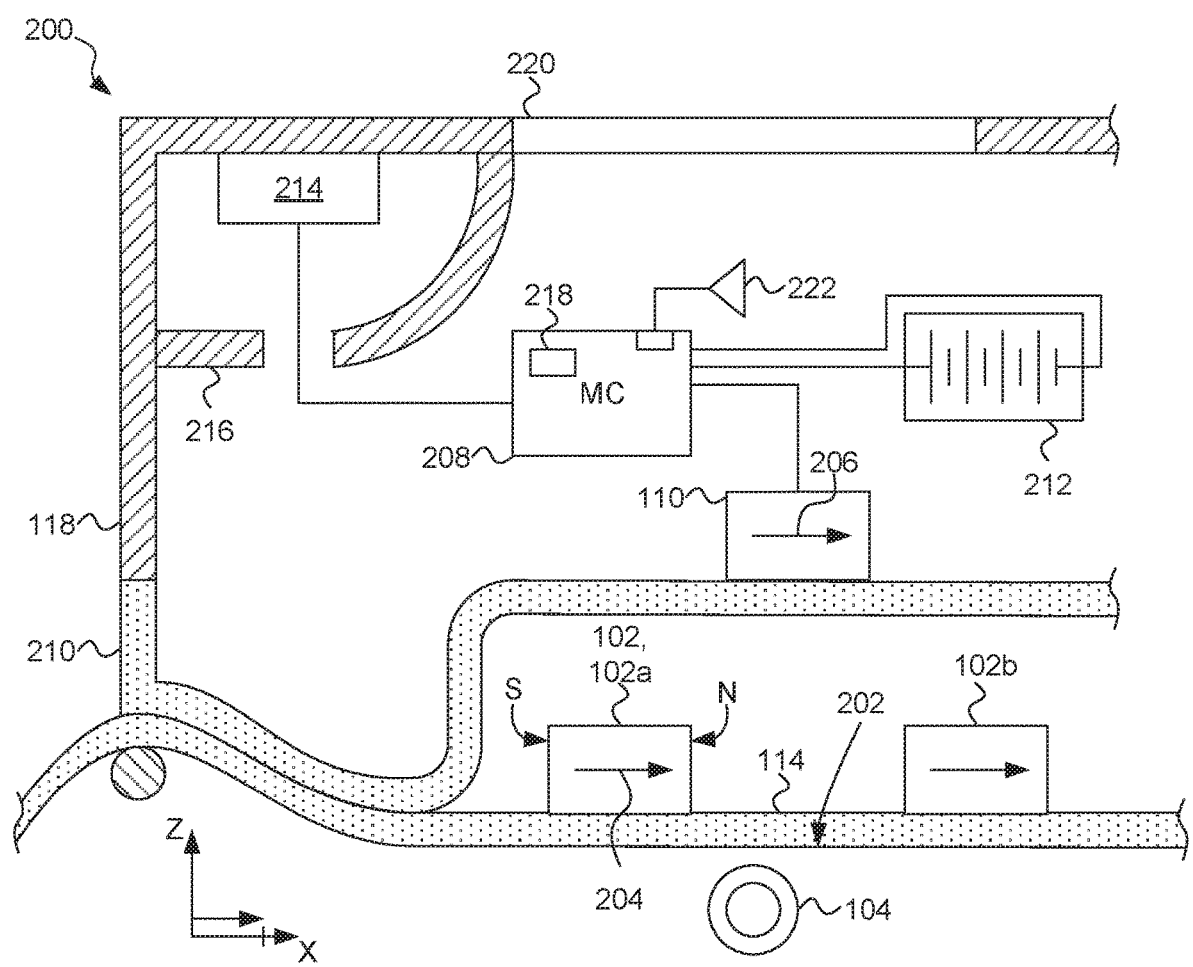
FIG. 2A is a diagram of a heart rate monitor during a diastolic portion of a user's heartbeat, according to an embodiment.
Figure 2B:
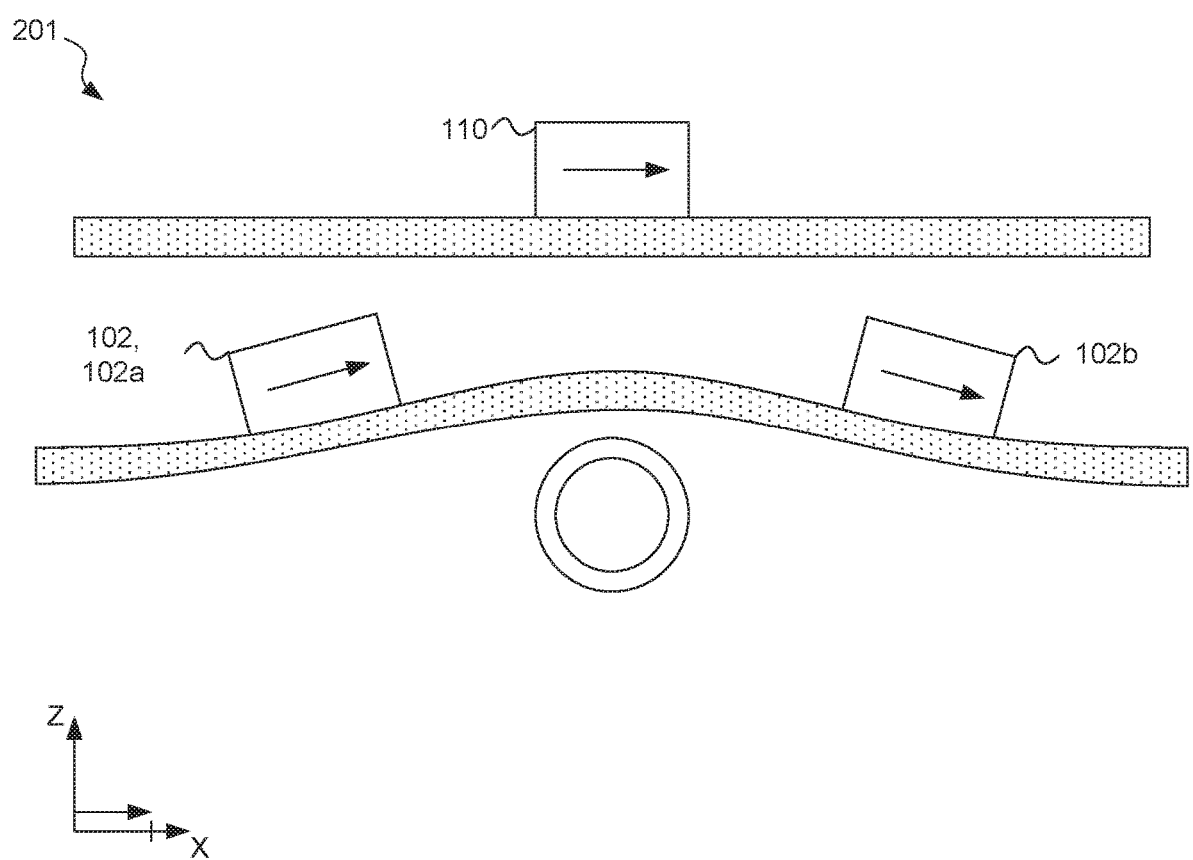
FIG. 2B is a diagram of a portion of the heart rate monitor of FIG. 1A during a systolic portion of the user's heartbeat, according to an embodiment.

FIG. 2A is a diagram of a heart rate monitor 200 during a diastolic portion of a user's heartbeat, according to an embodiment. FIG. 2B is a diagram 201 of a portion of the heart rate monitor 200 of FIG. 2A during a systolic portion of the user's heartbeat, according to an embodiment. Referring to FIGS. 2A and 2B, the heart rate monitor 200 can include a flexible membrane 114 configured to be held adjacent to a user's skin 202 at a location corresponding to an artery 104 subject to pulse movement. At least one magnet 102 having a magnetic axis 204 is disposed on the flexible membrane 114. By supporting the flexible membrane 114 and the at least one magnet 102 against the user's skin 202 over the artery 104, the at least one magnet 102 can be configured to physically tilt responsive to the pulse movement, whereby the magnetic axis 204 tilts. FIG. 2A shows a diastolic portion of the heartbeat when the artery 104 is contracted. The magnet(s) 102 tend to lie in plane with the user's skin 202. FIG. 2B shows a systolic portion of the heartbeat when the artery 104 expands under systolic pumping pressure from the heart. As can be seen, the magnet(s) 102 and corresponding magnetic axis 204 (axes) is (are) tilted up responsive to the pulse movement.

As used herein, the term magnetic axis 204 is defined relative to a magnet 102; that includes a north pole (indicated as N) and a south pole (indicated as S); such that the magnetic axis 204 is a line intersecting both the north pole and the south pole of the magnet 102.

The magnetometer 110 is configured to measure a magnetic field produced by the at least one magnet 102, the magnetometer 110 having a magnetic field measurement axis 206 along which the magnetic axis 204 tilt causes a change in measured magnetic field strength. The detected magnetic field strength varies according to the tilt angle of the magnetic axis 204 relative to to the measurement axis 206. A periodicity corresponding to the detected magnetic field strength corresponds to the systolic-diastolic rhythm, and thus serves as a measurement of heart rate.

Moreover, it can be appreciated that the difference between magnet(s) angles, expressed as a difference in maximum and minimum detected magnetic field strength, can be proportional to a difference between systolic and diastolic blood pressure, which can, it is contemplated, be related to gauge blood pressure of the user.

The arrangement depicted in FIGS. 2A and 2B can be especially useful for cases where the magnetometer 110 either does not have the ability to measure changes in magnetic field strength in the z-axis normal to the skin 202 of the user; or where the signal to noise ratio, sensitivity, or accuracy of z-axis measurement is inferior to measurements taken along the x-axis, which is nominally parallel to the magnetic axis (axes) 204 of the magnet(s) 102. This aspect can be leveraged to minimize or reduce z-axis height of the magnetometer 110 and/or to minimize or reduce z-axis height of the housing 118 (such as a portion of a smart watch band) that forms a portion of the heart rate monitor 200.

In some embodiments, the magnetic field measurement axis 206 can be selected to be momentarily parallel to the plane of the magnetic axis 204 of the at least one magnet 102 during a pulse period. This can occur once per period if the magnetic axis 204 is parallel to the measurement axis 206 either at diastole or at systole; or it can occur twice per period if the magnetic axis 204 is momentarily parallel to the magnetic field measurement axis 206 at a point other than maximum or minimum angular displacement (e.g., at a point in the period other than diastole or systole). In other embodiments (e.g., if the magnet 102 is at a different angular position along a curved skin surface from the magnetometer 110), the magnetic axis 204 is never parallel to the magnetic field measurement axis 206 during heart rate measurement.

Nevertheless, the measured magnetic field strength along the magnetic field measurement axis 206 will vary during the pulse period if the magnet(s) 102 is supported sufficiently close to the artery 104 that the magnet 102 tilts responsive to pulse.

As illustrated in FIGS. 2A, 2B, and 3, the at least one magnet 102 can include a plurality of magnets 102a, 102b disposed to cause at least two of the plurality of magnets 102a, 102b to physically tilt responsive to the pulse movement of the artery 104 and the skin 202. In some embodiments, there may be precisely two magnets 102a, 102b that are configured to align with the pulse point when the user dons the apparatus 200. In other embodiments, there may be three, four, or a large plurality of magnets 102a, 102b located along the flexible membrane 114, such that a gap between two of the magnets 102a, 102b will span the pulse measurement position over the artery 104. This can be used, for example, to improve tolerance for rotational displacement of the apparatus 200 around the user's wrist, improve tolerance to physical morphology differences between users, and/or allow for a loser fit of the flexible membrane 114.

Referring especially to FIG. 2A, the heart rate monitor 200 can include a microcontroller 208 operatively coupled to the magnetometer 110. The housing 118 can be configured to support the magnetometer 110 and configured to urge the flexible membrane 114 against the user's skin 202. The housing 118 can include a magnetically transparent housing portion 210 selected to pass the magnetic field produced by the magnet(s) 102 to the magnetometer 110. For example, the magnetically transparent housing portion 210 can be formed from a non-ferromagnetic material such as a plastic or aluminum. Additionally or alternatively, the housing 118 can be configured to support the magnetometer 110 between the housing 118 and the magnet 102 (configuration not shown). In this configuration, it can still be preferable for the housing 118 to be non-ferromagnetic in order to avoid distorting magnetic field lines from the magnet(s) 102.

The heart rate monitor 200 can further include a battery 212 contained within the housing 118 and configured to provide sufficient power to maintain function of the pulse sensor 200 for at least 24 hours. In some embodiments, the microcontroller 208 can go to sleep and receive motion and/or heart rate data responsive to a predetermined interval. When motion and/or heart rate is relatively constant or has a low value, the microcontroller 208 can be programmed to go back to sleep. When motion and/or heart rate data has changed since a previous sample, the microcontroller 208 can be programmed to wake up and track heart rate and motion, and output data corresponding to heart rate and motion. When motion decreases and heart rate drops, the microcontroller 208 can be programmed to go back to sleep. The combination of a low power microcontroller and the inherently low power consumption of the magnetometer 110 used for heart rate detection can enable the battery 212 to provide sufficient power to maintain function of the pulse sensor 200 for at least one week. This is possible with current battery technology owing to the very low power consumption of the magnetometer 110 compared to an optical pulse sensor.

The heart rate monitor 200 can further include a motion sensor 214 operatively coupled to the microcontroller 208. For example, the motion sensor 214 can include an accelerometer or a second magnetometer configured to sense an ambient magnetic field that is substantially stationary relative to movements of the user. In the "second magnetometer" embodiment, movement of the user through the earth's magnetic field and/or other ambient magnetic fields is sensed. In the second magnetometer embodiment, the heart rate monitor 200 can further include a magnetic shield 216 configured to shield the second magnetometer 214 from changes in magnetic field strength corresponding to movement of the magnet 102.

In another embodiment the motion sensor 214 can be integral with the magnetometer 110 and can consist essentially of a magnetometer axis (e.g., along the y-axis into the plane of the drawing, FIGS. 2A and 2B) that is transverse to the magnetic axis 204. This approach results in partial confounding of movement with the pulse motion of the magnet(s) 102, but can be useful for parts reduction. In another embodiment, the motion sensor 214 can be integral with the magnetometer 110, and the motion sensor can consist essentially of an accelerometer.

The heart rate monitor 200 can further include a non-transitory computer-readable medium 218 contained within the microcontroller 208 or separate from the microcontroller and operatively coupled to the microcontroller 208. In an embodiment, the non-transitory computer-readable medium 218 carries microcontroller instructions configured to cause the microcontroller 208 to receive data or a signal from the magnetometer 110, receive detected movement information from the motion sensor 214, and filter the data or signal from the first magnetometer responsive to the detected movement.

The filtering is described more fully in conjunction with FIG. 3 below.

The heart rate monitor 200 can further include an electronic display 220 operatively coupled to the microcontroller 208. The microcontroller 208 can be configured to calculate a most likely pulse rate and to cause the electronic display 220 to display the most likely pulse rate.

The heart rate monitor 200 can further include a radio 222 operatively coupled to or contained at least partially within the microcontroller 208. The microcontroller 208 can be configured to calculate a most likely pulse rate and to cause the radio 222 to transmit the most likely pulse rate, for example to a smart phone (not shown) running a fitness application that tracks the pulse rate.

Still referring to FIGS. 2A and 2B, according to an embodiment, the heart rate monitor 200 includes a flexible membrane 114 configured to be held adjacent to a user's skin 202 at a location corresponding to an artery 104 subject to pulse movement, at least one magnet 102 disposed on the flexible membrane 114 and configured to move responsive to the pulse movement, and a magnetometer 110 configured to measure variations in a magnetic field from the at least one magnet responsive to the pulse movement.

Other embodiments include positioning the magnetic axis 204 in a different orientation relative to the user's skin surface 202, than what is depicted in FIGS. 2A and 2B. For example, the magnet(s) 102 can be disposed to have a vertical magnetic axis, such that magnetic axis 204 is substantially normal transverse to the user's skin surface 202 (e.g. up to substantially perpendicular to the user's skin surface 202), and the magnetometer 110 can be configured to have a measurement axis 206 that measures variations in magnetic field strength along a vertical axis substantially parallel to the magnetic axis. Although advantages corresponding to overcoming z-axis precision, signal-to-noise, or size may be lost, such a (normal) alignment of magnetic axis and magnetic measurement axis was found by the inventors to work.

The motion sensor 214 is configured to detect movement of the human. The inventors have found that detected movement can provide data for inferring a change in heart rate. For example, an increased amount of movement may typically correspond to an increase in heart rate, and conversely a decreased amount of movement may typically correspond to a decrease in heart rate. The predictive nature of movement can be used to select from between several frequency candidates in successive signals from the magnetometer 110, any of which may correspond to the true heart rate.

The microcontroller 208 operatively coupled to the magnetometer 110 and the motion sensor 214 can include the non-transitory computer-readable medium 218 carrying microcontroller instructions. The instructions can be selected to cause the microcontroller 208 to receive data or a signal from the magnetometer 110, receive detected movement information from the motion sensor 214, filter the data or signal from the first magnetometer responsive to the detected movement, and output heart rate data corresponding to the filtered data or signal from the first magnetometer 110.

The approach to filtering is described in greater detail below.

FIG. 3 is a flow chart of a method 300 for detecting a heart rate, according to an embodiment. According to the method 300, a magnet is supported adjacent to the skin of a user in step 302. In step 304, a periodic physical impulse is received by the magnet responsive to arterial movement during systole and diastole. Proceeding to step 306, the magnet undergoes a periodic tilting motion responsive to the periodic physical impulse corresponding to systole and diastole. In step 308, a magnetometer detects, along an axis parallel to the person's skin, a periodic change in the strength of the magnetic field produced by the magnet. In step 310, a signal or data corresponding to a periodicity of the detected periodic change in the strength of the magnetic field is output. The output signal or data can correspond to a heart rate of the person.

Figure 4:
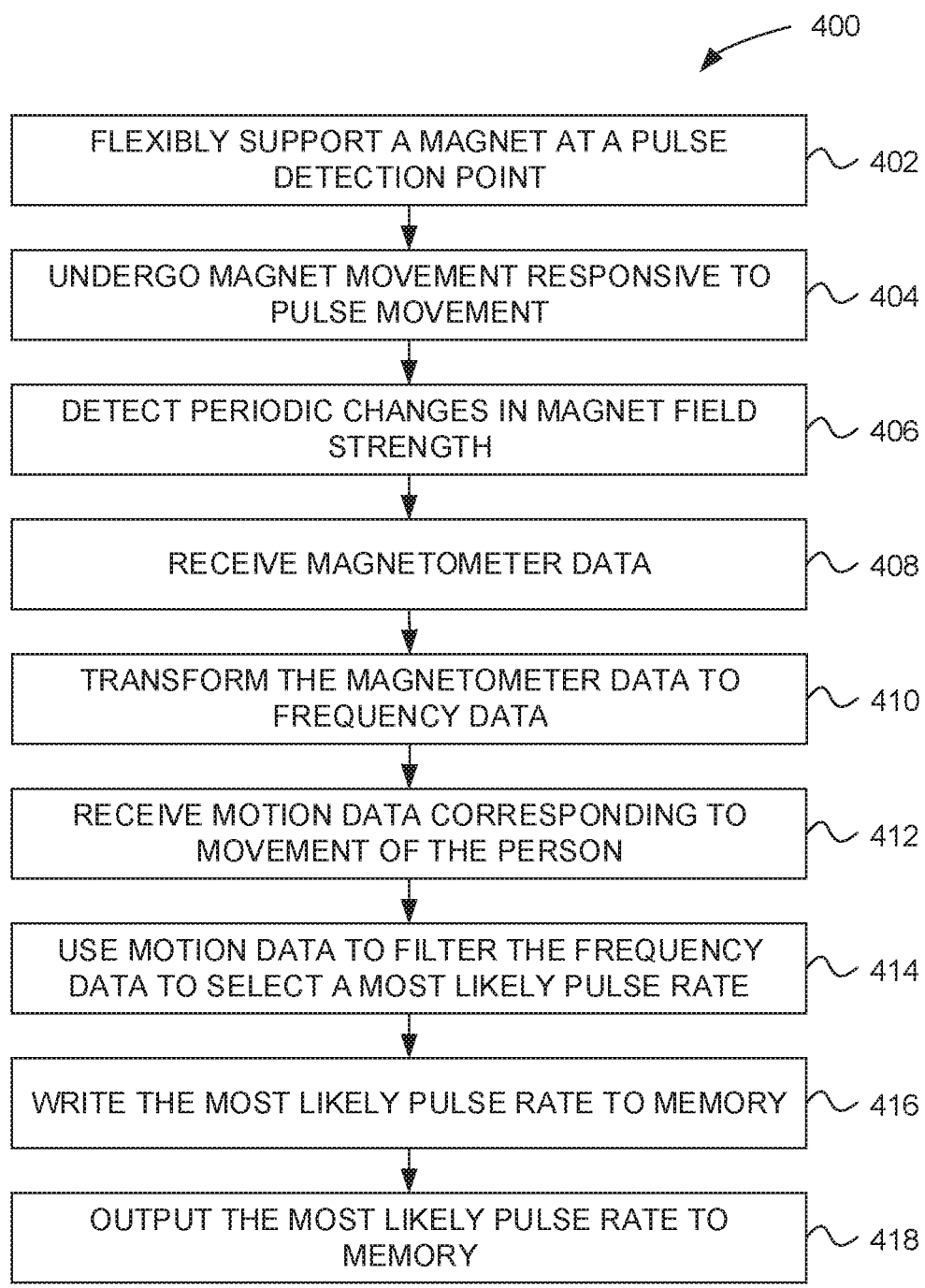
FIG. 4 is a flow chart of a method for tracking the heart rate of a person, according to an embodiment.

FIG. 4 is a flow chart of a method 400 for tracking the heart rate of a person, according to an embodiment. In step 402 a magnet is flexibly supported adjacent to a pulse detection location of a person. According to an embodiment, flexibly supporting a magnet adjacent to a pulse detection location of a person includes supporting a flexible membrane adjacent to the pulse detection location and supporting the magnet with the flexible membrane. For example, the flexible membrane can support the magnet adjacent to a pulse detection location on a wrist of the person. The inventors contemplate several alternative pulse measurement locations. In other examples, the flexible membrane can support the magnet adjacent to a pulse detection location on a foot or ankle of the person, adjacent to a pulse detection point on the neck of the person, or adjacent to the temple of the person.

Proceeding to step 404, the magnet undergoes movement responsive to pulse movement of the person. As described above, the movement is responsive to expansion and contraction of an adjacent artery, and especially a peripheral artery, respectively corresponding to systolic and diastolic pressure pulses from the heart. As described above, several modes of movement and detection are contemplated. In a preferred embodiment, the magnet tilts responsive to arterial pulsing, and corresponding magnetic field strength is detected along an axis substantially parallel to the skin surface of the person.

In step 406, a magnetometer is operated to detect periodic changes in magnetic field strength from the magnet, the periodic changes in magnetic field strength corresponding to the movement of the magnet and the pulse movement of the person.

Proceeding to step 408, a microcontroller receives magnetometer data including the periodic changes in magnetic field strength from the magnet. The microcontroller can, as shown in step 410, transform the magnetometer data to produce frequency data. For example, transforming the frequency data can include performing a Fourier transform such as a Fast Fourier Transform (FFT).

In step 412, the microcontroller receives motion data corresponding to movement of the person. The motion data can be produced by an accelerometer or another motion sensing device. In one example, the motion sensing device can include another magnetometer or another axis of the pulse-sensing magnetometer, wherein the motion data corresponds to motion of the person relative to far field sources, such as the earth's magnetic field.

In step 414, the motion data is used to filter the frequency data to select a frequency most likely to correspond to a pulse rate of the person. For example, using the motion data to filter the frequency data can include writing the frequency data to memory, writing the motion data to memory, comparing the motion data to previous motion data, determining the likelihood of a change in pulse rate responsive to the compared motion data, comparing the frequency data to previous frequency data, and identifying a high magnitude frequency domain point most likely to correspond to the pulse rate.

The method 400 can further include step 416, wherein the most likely pulse rate is written to memory, and step 418, wherein the most likely pulse rate is output. For example, step 418 can include wirelessly transmitting the most likely pulse rate to a personal electronic device. The personal electronic device can be configured to run a fitness or health application that uses the pulse rate. Additionally or alternatively, outputting the most likely pulse rate can include displaying the most likely pulse rate on an electronic display.

Figure 5A:
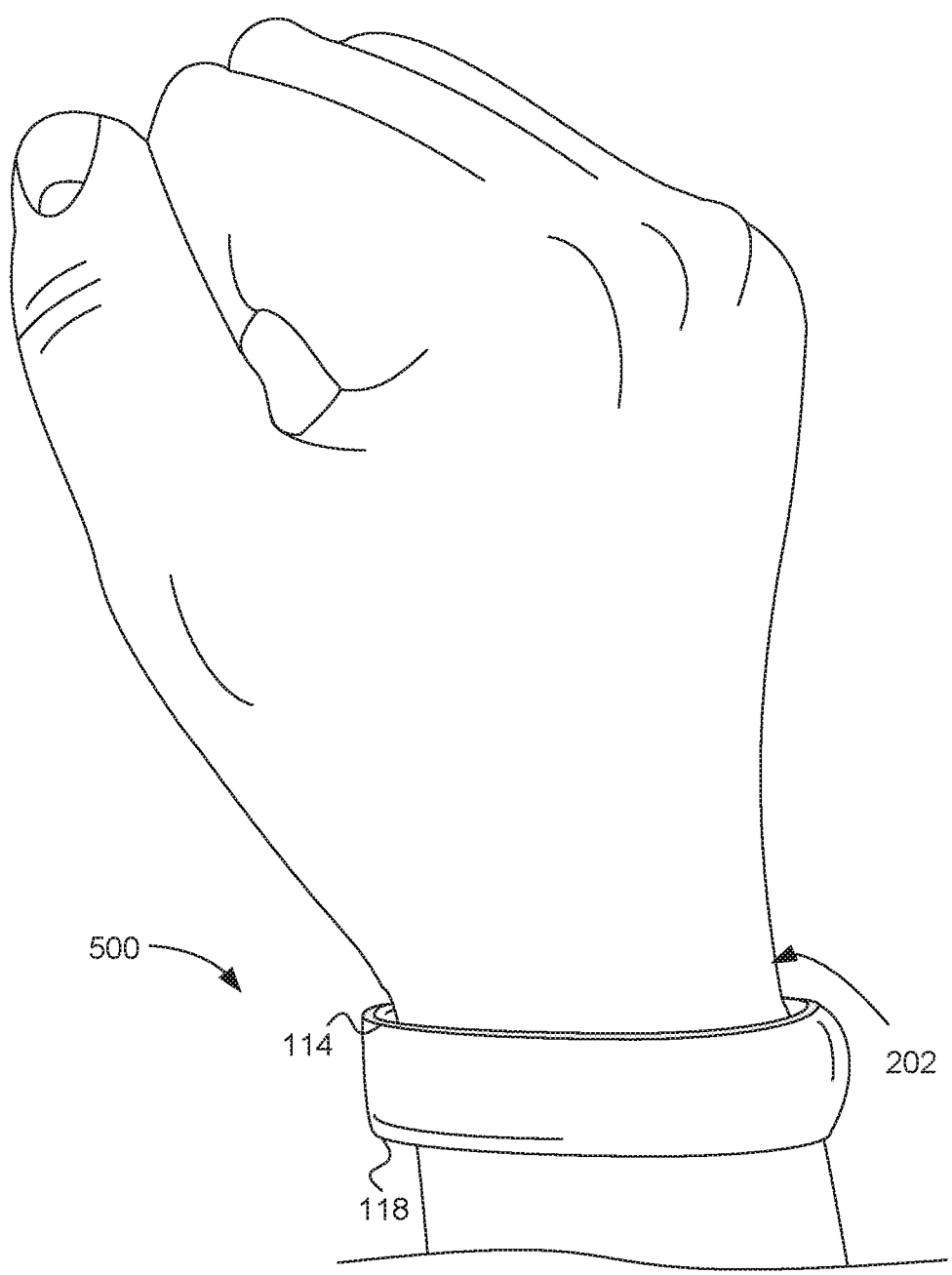
FIG. 5A is a perspective view of a pulse sensor configured as a wristband, according to an embodiment.

FIG. 5A is a perspective view of a pulse sensor 500 configured as a wristband, according to an embodiment. In another embodiment, the pulse sensor 500 can be configured as a hat or visor band configured to receive pulse movement from a human head. In another embodiment, the pulse sensor 500 can be configured as a sock or a shoe configured to receive pulse movement from a human ankle or foot. Other embodiments can include articles configured to be held against other areas of human skin subject to pulse movement.

Figure 5B:
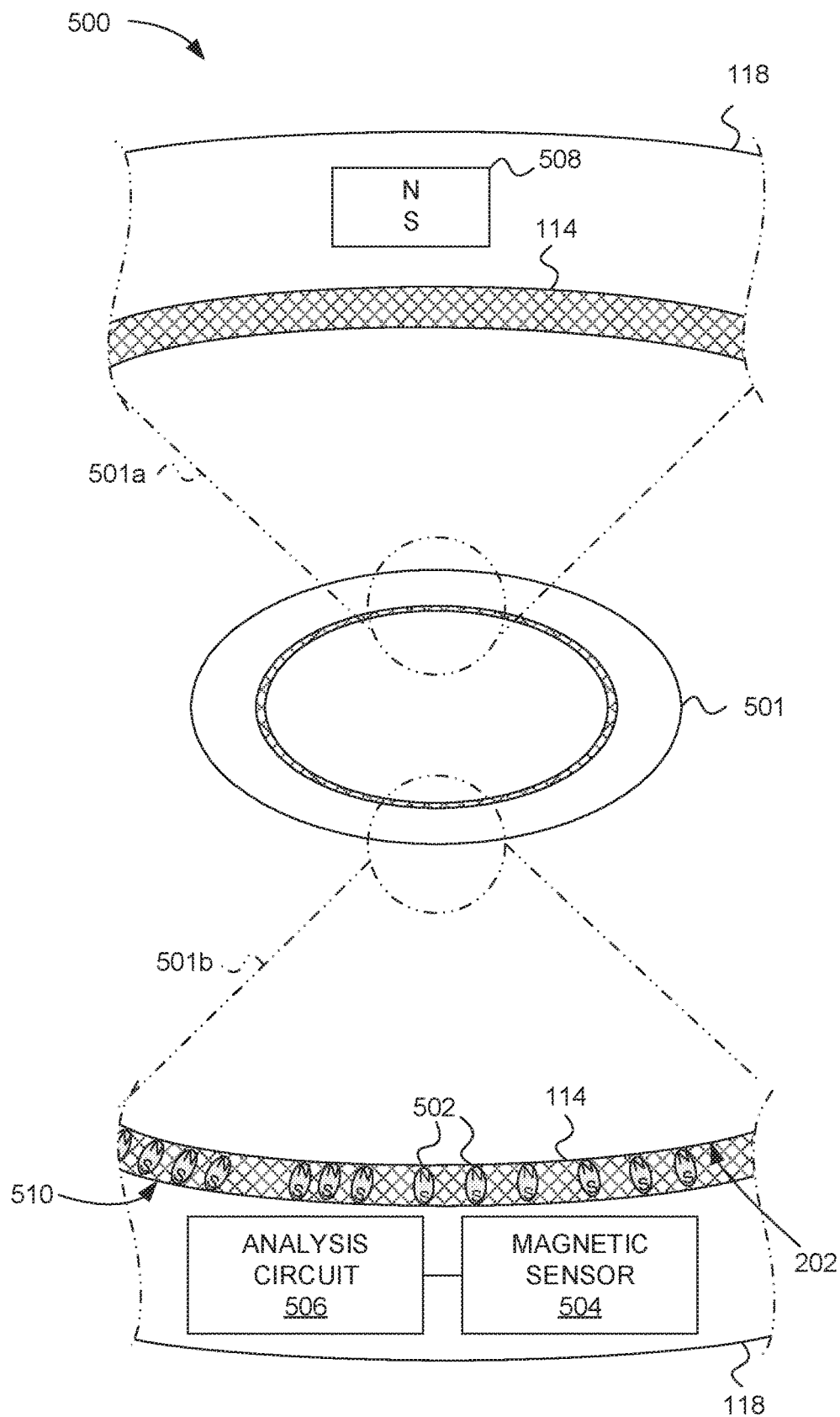
FIG. 5B is a sectional view and partial sectional views of the pulse sensor 100 of FIG. 5A, according to an embodiment.

FIG. 5B is a sectional diagram 501 with partial sectional views 501a, 501b of the pulse sensor 500 shown in FIG. 5A, according to an embodiment. With reference to FIGS. 5A and 5B, a flexible substrate 114 is configured for support against a human skin surface 202. The pulse sensor 500 includes a plurality of aligned magnetic dipoles 502 supported by the flexible substrate 114. A magnetic sensor 504 is configured to detect magnetic fields emitted by the plurality of magnetic dipoles 502. The magnetic sensor 504 can be a magnetometer, for example. An analysis circuit 506 is operatively coupled to the magnetic sensor 504.

The analysis circuit 506 can be configured to receive a sequence of data from the magnetic sensor 504. The sequence of data can include a component corresponding to changes in position of a portion of the plurality of magnetic dipoles 502, for example, the changes in position of the portion of the plurality of magnetic dipoles 502 corresponding to a pulse movement of the human skin surface 202. The analysis circuit 506 can be configured to output pulse chart data corresponding to the sequence of data, to determine a heart rate and output the heart rate to a data register.

Optionally, the pulse sensor 500 can include a poling magnet 508 configured to pole the plurality of magnetic dipoles 502 into alignment. The poling magnet 508 can include a permanent magnet configured to maintain a substantially constant magnetic field across each of the plurality of magnetic dipoles 502. Alternatively the poling magnet 508 can include an electromagnet. The electromagnet can be configured to maintain a substantially constant magnetic field across each of the plurality of magnetic dipoles 502 or can be configured to apply a periodically reversing poling field to the plurality of magnetic dipoles 502.

The plurality of magnetic dipoles 502 can consist essentially of high coercivity magnetic particles whose pole orientations are aligned by an external magnet as they are cured into the flexible substrate 114 while the flexible substrate 114 is curing. In this case, the plurality of magnetic dipoles 502 are held in magnetic alignment by a cross-linked component of the flexible substrate 114. Additionally or alternatively, the plurality of magnetic dipoles 502 can be placed in pole aligned orientation by assembling them onto the flexible substrate 114 with a pick-and-place machine.

Alternatively, the plurality of magnetic dipoles 502 can consist essentially of low coercivity ferromagnetic particles whose pole orientation is induced by an applied magnetic field. As described above, the pulse sensor 500 can include the poling magnet 508 configured to hold the plurality of ferromagnetic particles in magnetic alignment as magnetic dipoles 502. The poling magnet 508 can include a permanent magnet. The poling magnet 508 can be configured to maintain a substantially constant magnetic field across each of the plurality of magnetic dipoles 502. The poling magnet 508 can include an electromagnet. The electromagnet can be configured to apply a field with periodically reversing magnetic pole to the plurality of magnetic dipoles 502.

The sequence of data output from the magnetic sensor 504 to the analysis circuit 506 can include data corresponding to the periodically reversing magnetic field, convert the sequence of data to baseband data that includes the component corresponding to changes in position of the portion of the plurality of magnetic dipoles 502 corresponding to a pulse movement of the human skin surface 202. The plurality of magnetic dipoles 502 can be configured to rotate responsive to the periodically reversing poling field and to maintain magnetic polarity in the periodically reversing poling field.

The plurality of magnetic dipoles 502 can be held in alignment by a cross-linked component of the flexible substrate 114. The alignment of the magnetic dipoles 502 can be formed by poling the magnetic dipoles 502 carried by a precursor of the flexible substrate 114 and cross-linking the cross-linked component to hold the plurality of magnetic dipoles 502 in net magnetic alignment. Additionally or alternatively, the plurality of magnetic dipoles 502 can be held in alignment by the flexible substrate 114 and/or assembled onto the flexible substrate 114 by a pick-and-place machine.

The magnetic dipoles 502 can carry a net magnetic alignment as a group. Individual magnetic dipoles can carry respective magnetic axes that differ from the net magnetic alignment. The magnetic dipoles 502 can be aligned along a Cartesian axis, aligned along respective radial axes, aligned along hyperbolically varying axes in at least one plane, and/or aligned with respective axes that are substantially normal to the flexible substrate 114.

The magnetic sensor 504 can include a sensor configured to sense a magnetic field strength along at least one axis parallel to at least a portion of the magnetic dipole alignment. Optionally, the magnetic sensor 504 can be configured to sense magnetic field strength along a plurality of axis. For example, the magnetic sensor 504 can include an X-axis magnetic sensor configured to sense a magnetic field component along an X-axis, a Y-axis magnetic sensor configured to sense a magnetic field component along a Y-axis, and a Z-axis magnetic sensor configured to sense a magnetic field component along a Z-axis. The X-, Y-, and Z-axes can be defined with respect to a sensor circuit assembly and/or can be defined with respect to the plurality of aligned magnetic dipoles 502.

The magnetic sensor 504 can include at least one sensor aligned relative to the aligned magnetic dipoles 502 and a magnetic sensor array configured to sense magnetic field components at a plurality of locations in a sensor array.

The magnetic sensor 504 can be configured to sense one or more magnetic field components less than $10^{-3}$ as strong as the earth's magnetic field. In another embodiment, the magnetic sensor 504 can be configured to sense one or more magnetic field components less than $10^{-6}$ as strong as the earth's magnetic field.

The magnetic sensor 504 can be arranged as a plurality of sensor modules, each sensor module being configured to sense a magnetic field along a plurality of sensing axes.

The analysis circuit 506 can be configured to receive a sequence of data from the magnetic sensor 504. Each datum in the sequence of data can correspond to magnetic field strength along each of three axes. The analysis circuit 506 can be configured to transform each datum by calculating a square root of a sum of squares of the data corresponding to the magnetic field strength along each of three axes. Additionally or alternatively, the analysis circuit 506 can be configured to output the transformed data to a data buffer.

The pulse sensor 500 can include the housing 118 configured to carry the flexible substrate 114, the magnetic sensor 504, and the analysis circuit 506. The housing 118 can be configured to be worn around a human wrist, as shown in FIG. 5A. The flexible substrate 114 can be elastomeric. The housing 118 can include a suspension, such as hydrogel, operatively coupled to the flexible substrate 114, the suspension being configured to urge the flexible substrate 114 against the human skin surface 202.

The pulse sensor 500 can further include an elastomeric foam disposed to press against an outside surface 510 of the flexible substrate 114, the elastomeric foam being configured to urge the flexible substrate 114 carrying the plurality of magnetic dipoles 502 against the human skin surface 202.

Figure 6:
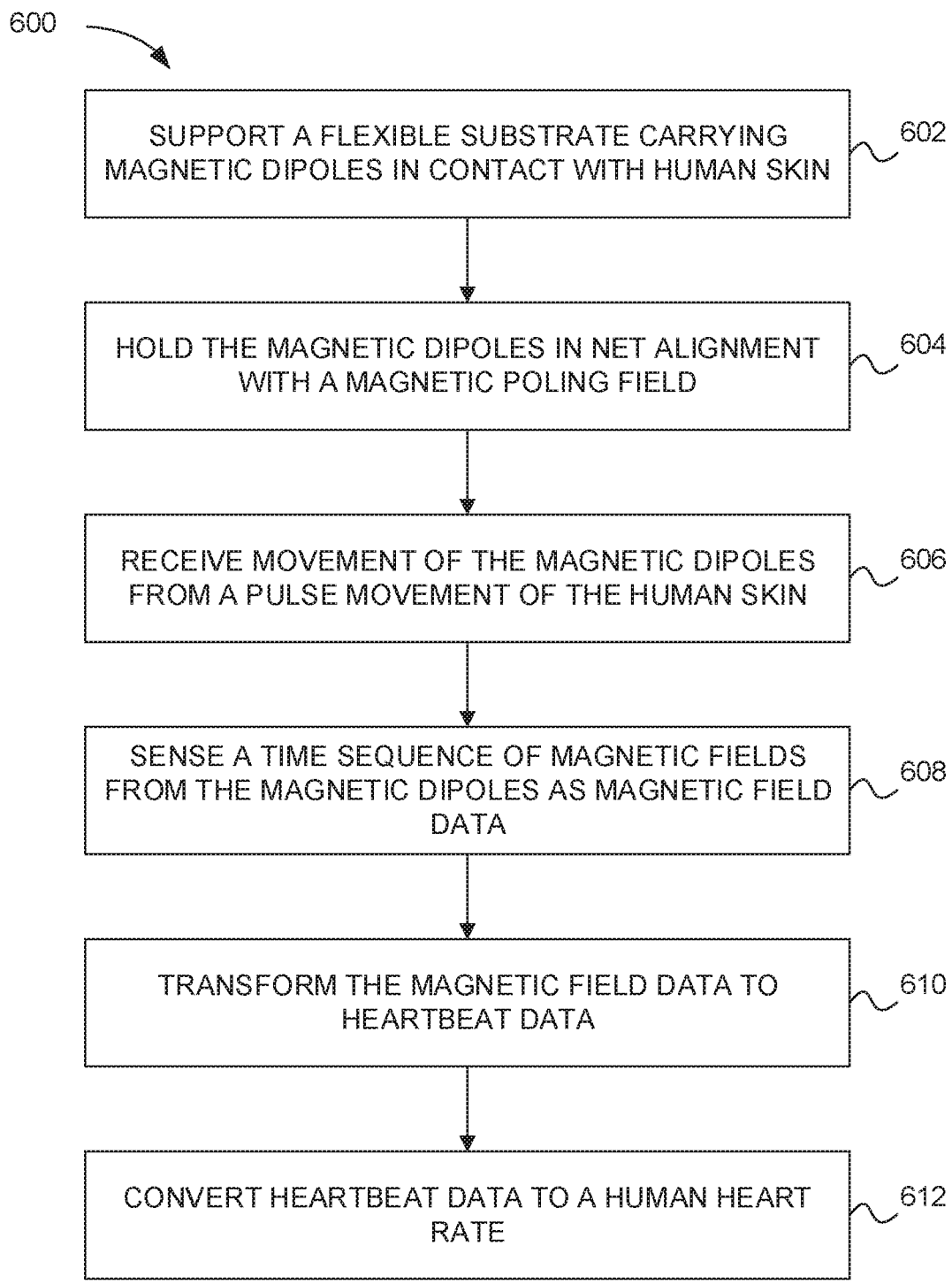
FIG. 6 is a flowchart showing a method for detecting a human pulse, according to an embodiment.

FIG. 6 is a flowchart showing a method 600 for detecting a human pulse, according to an embodiment. The method 600 begins with step 602, in which a flexible substrate carrying aligned magnetic dipoles is held against a human skin surface. The flexible substrate is particularly held against a portion of the skin subject to motion caused by a human pulse. For example, the flexible substrate with magnetic dipoles can be held against an artery in a wrist, or against a carotid artery in the neck.

Optionally, the method 600 can include step 604, wherein the plurality of magnetic dipoles are held in net magnetic alignment by supporting a magnet near the plurality of magnetic dipoles. The magnet forms a magnetic poling field across the plurality of magnetic dipoles that causes the magnetic dipoles to rotate into alignment. According to an embodiment, aligned magnetic dipoles can be formed as net magnetic dipoles. In other words, the magnetic dipoles can be aligned to an average axis, but individual magnetic particles (dipoles) can be off-axis or even antiparallel to the average axis.

In alternative to step 604, the magnetic dipoles can be aligned during manufacture of the pulse sensor. For example, the dipoles can be poled while a polymer is cross-linked around the dipoles to hold them in place. Alternatively, the dipoles can be applied to the flexible substrate in alignment, such as by a pick-and-place machine.

Proceeding to step 606, physical movement of a portion of the magnetic dipoles from the human skin surface is received, the physical movement being a pulse movement of the human skin surface.

In step 608, magnetic field data is sensed. For example, the magnetic field data can include measurement of a time sequence of magnetic fields. The time sequence can include a component corresponding to motion of the aligned magnetic dipoles caused by the human pulse.

Proceeding to step 610, the magnetic field data is transformed to heartbeat data corresponding to the sensed human pulse. The method 600 can include step 612, wherein the heartbeat data is converted to a human heart rate.

EXAMPLES

Figure 7:
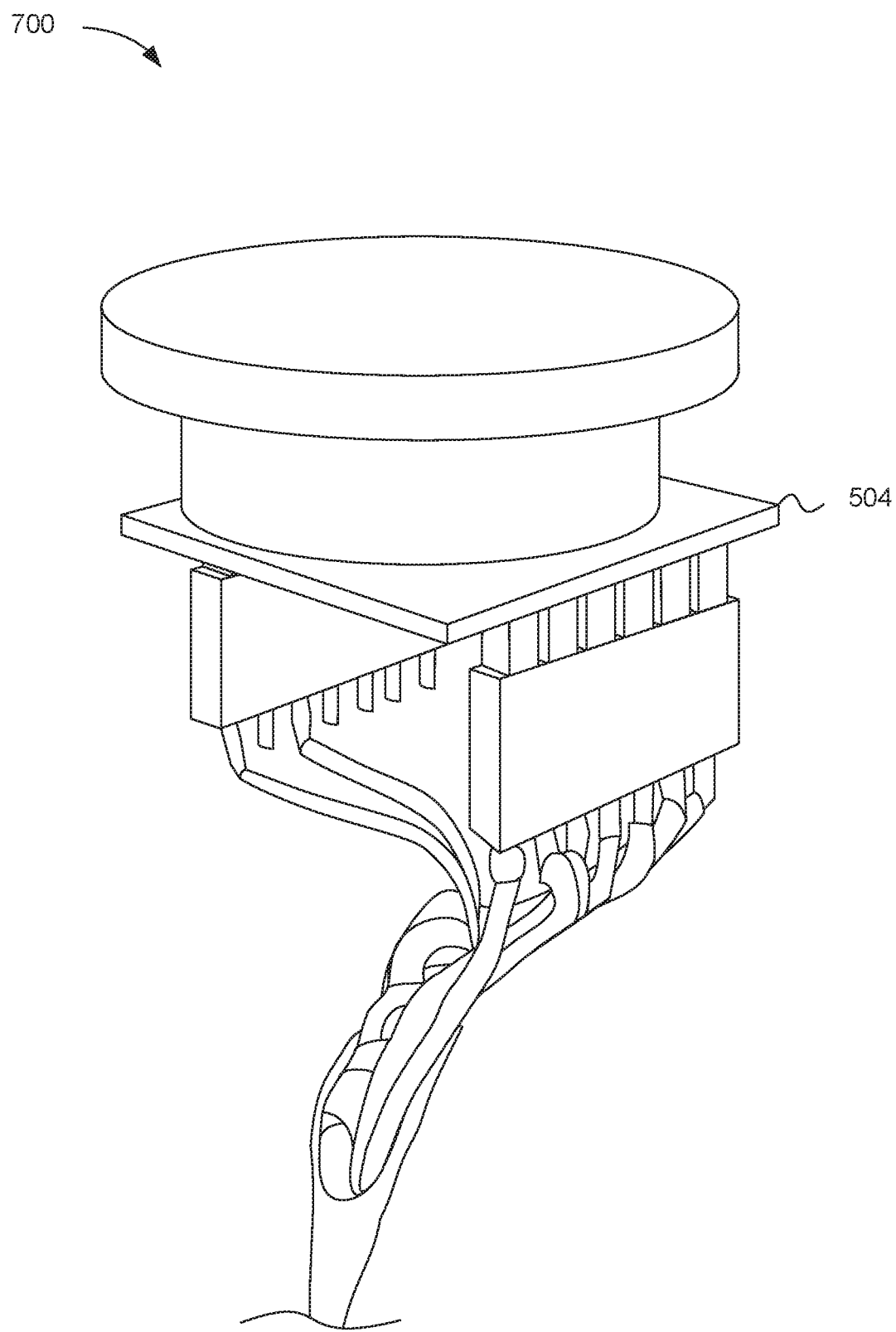
FIG. 7 is a view of a magnetic sensor used in an experiment reported in the Examples section, according to an embodiment.
Figure 8:
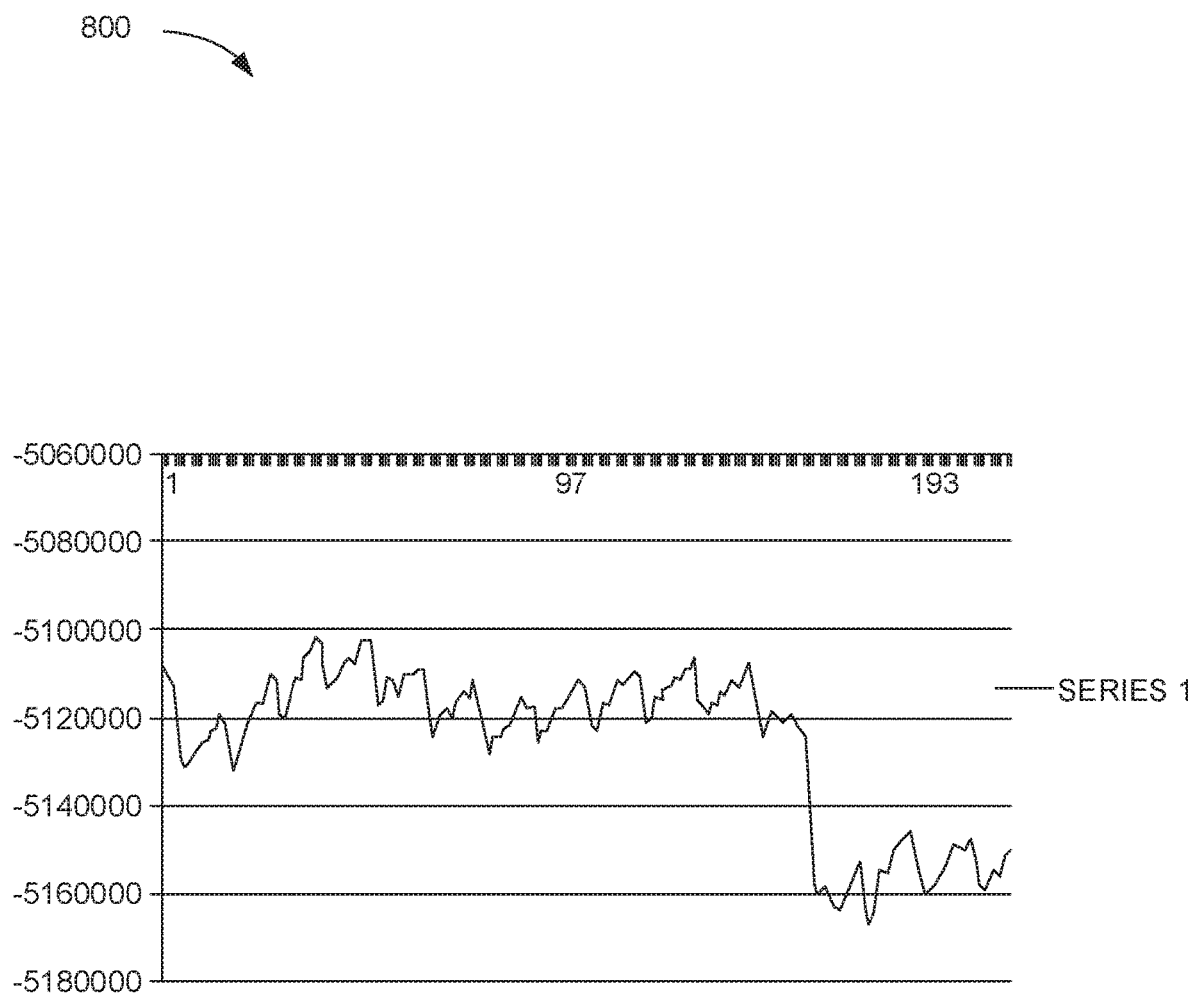
FIG. 8 is a plot of heartbeat data from the experiment described in the Examples section, according to an embodiment.

Specific embodiments may be made by reference to the following examples:
Objective:
The objective of this study is to determine the technical feasibility of detecting human pulse at the wrist by means of magnetic sensors using a novel approach in which what is detected is perturbations to a reference magnetic field created by arterial palpation, i.e. the expansion/contraction of the artery cause by the bloods pulsation.
Approach:
The approach used in this study is to embed magnetic particles into an elastomeric substrate. The magnetic particles were formed by crushing a permanent magnet. The magnetic poles of the particles were aligned while the substrate was cured by exposing them to a strong external magnet. The resulting elastomeric membrane was then stretched across a PVC cylindrical cross-section and the magnetic sensor module was mounted on the opposite end of the PVC cylinder such that the sensor that is perpendicular to the membrane is approximately 2 mm from the membrane sensing down towards the membrane. A view of the sensor 504 is shown in FIG. 7. The sensor module 700 was connected by ribbon cable to a circuit board with power, control and I/O capabilities.
Results:
The sensor was pressed to the wrist at the radial artery. Samples were taken at a frequency 16.6 Hz for 12 s. The resulting time series clearly show a pulse averaging approximately 75 beats per minute. Data plots 800, 900 are shown in FIGS. 8 and 9. The pulse was then independently estimated to be approximately 75 bpm, which verified the data.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:
1. A heart rate monitor, comprising:
a flexible membrane configured to be held adjacent to a user's skin at a location corresponding to an artery subject to pulse movement;
at least one magnet disposed on the flexible membrane and configured to move responsive to the pulse movement;

a magnetometer configured to measure variations in a magnetic field from the at least one magnet responsive to the pulse movement;

a motion sensor configured to detect movement of the human; and a microcontroller operatively coupled to the magnetometer and the motion sensor, the microcontroller including a non-transitory computer-readable medium carrying microcontroller instructions configured to cause the microcontroller to:

receive data from the magnetometer;

receive detected movement information from the motion sensor;

transform the data from the magnetometer to produce frequency data;

receive, with the microcontroller, motion data corresponding to the movement of the human; and use the motion data to filter the frequency data to select a frequency most likely to correspond to a pulse rate of the person;

wherein using the motion data to filter the frequency data further comprises:

writing the frequency data to memory;

writing the motion data to memory;

comparing the motion data to previous motion data;

determining the likelihood of a change in pulse rate responsive to the compared motion data;

comparing the frequency data to previous frequency data; and identifying a high magnitude frequency domain point most likely to correspond to the pulse rate.

2. The heart rate monitor of claim 1, wherein the at least one magnet has a magnetic axis defined as a line intersecting both the north pole and the south pole of the magnet, and the magnet being configured to move further comprises the magnet being configured to physically tilt responsive to the pulse movement, whereby the magnetic axis tilts; and wherein the magnetometer has a magnetic field measurement axis along which the magnetic axis tilt causes a change in measured magnetic field strength.

3. The heart rate monitor of claim 2, wherein the magnetic field measurement axis is angled to be momentarily parallel to the plane of the magnetic axis of the at least one magnet during a pulse period.

4. The heart rate monitor of claim 2, further comprising:

a housing configured to support the magnetometer and configured to urge the flexible membrane against the user's skin.

5. The heart rate monitor of claim 4, further comprising:

a battery contained within the housing and configured to provide sufficient power to maintain function of the pulse sensor for at least 24 hours.

6. The heart rate monitor of claim 1, wherein the motion sensor comprises an accelerometer.

7. The heart rate monitor of claim 1, wherein the motion sensor comprises a second magnetometer configured to sense an ambient magnetic field that is substantially stationary relative to movements of the user.

8. The heart rate monitor of claim 7, further comprising a magnetic shield configured to shield the second magnetometer from changes in magnetic field strength corresponding to movement of the magnet.

9. The heart rate monitor of claim 2, further comprising: an electronic display operatively coupled to the microcontroller.

10. The heart rate monitor of claim 2, further comprising:

a radio operatively coupled to or contained at least partially within the microcontroller;

wherein the microcontroller is configured to calculate a most likely pulse rate and to cause the radio to transmit the most likely pulse rate.

11. A method for tracking the heart rate of a person, comprising:

flexibly supporting a magnet adjacent to a pulse detection location of a person, whereby the magnet undergoes movement responsive to pulse movement of the person;

operating a magnetometer to detect periodic changes in magnetic field strength from the magnet, the periodic changes in magnetic field strength corresponding to the movement of the magnet and the pulse movement of the person; and receiving, with a microcontroller, magnetometer data including the periodic changes in magnetic field strength from the magnet;

transforming the magnetometer data to produce frequency data;

receiving, with the microcontroller, motion data corresponding to movement of the person; and using the motion data to filter the frequency data to select a frequency most likely to correspond to a pulse rate of the person;

wherein using the motion data to filter the frequency data further comprises:

writing the frequency data to memory;

writing the motion data to memory;

comparing the motion data to previous motion data;

determining the likelihood of a change in pulse rate responsive to the compared motion data;

comparing the frequency data to previous frequency data; and identifying a high magnitude frequency domain point most likely to correspond to the pulse rate.

12. The method of claim 11 for tracking the heart rate of a person, further comprising:

supporting the magnet adjacent to the skin of the person;

whereby the magnet receives a periodic physical impulse with the magnet responsive to arterial movement during systole and diastole;

wherein the movement of the magnet includes a periodic tilting motion of the magnet responsive to the periodic physical impulse corresponding to systole and diastole;

wherein operating the magnetometer includes detecting a periodic change in the strength of the magnetic field produced by the magnet along an axis parallel to the person's skin; and outputting a signal or data corresponding to a periodicity of the detected periodic change in the strength of the magnetic field;

whereby the output signal or data corresponds to a heart rate of the person.

13. The method of claim 11 for tracking the heart rate of a person, wherein transforming the frequency data includes performing a Fourier Transform.

14. The method of claim 11 for tracking the heart rate of a person, further comprising:

outputting the pulse rate by at least one of the steps of wirelessly transmitting the pulse rate to a personal electronic device, and displaying the pulse rate on an electronic display.

15. The method of claim 11 for tracking the heart rate of a person, wherein flexibly supporting a magnet adjacent to a pulse detection location of a person further comprises:

supporting a flexible membrane adjacent to the pulse detection location; and supporting the magnet with the flexible membrane.

16. A pulse sensor, comprising:

a flexible substrate configured for support against a human skin surface;

a plurality of aligned magnetic dipoles supported by the flexible substrate adjacent to a pulse detection location of a person, whereby the plurality of aligned magnetic dipoles undergo movement responsive to pulse movement of the person;

a magnetic sensor configured to detect periodic changes in magnetic fields emitted by the plurality of magnetic dipoles corresponding to the movement of the magnetic dipoles and the pulse movement of the person;

an analysis circuit operatively coupled to the magnetic sensor; and a magnet configured to pole the plurality of magnetic dipoles:

wherein the alignment of the plurality of dipoles is caused by the magnet;

wherein the magnet includes an electromagnet;

wherein the electromagnet is configured to apply a periodically reversing magnetic poling field to the plurality of magnetic dipoles; and wherein the sequence of data output from the magnetic sensor to the analysis circuit includes data corresponding to the periodically reversing magnetic field, convert the sequence of data to baseband data that includes the component corresponding to changes in position of the portion of the plurality of magnetic dipoles corresponding to a pulse movement of the human skin surface.

17. The pulse sensor of claim 16, wherein the analysis circuit is configured to receive a sequence of data from the magnetic sensor;

wherein the sequence of data includes a component corresponding to changes in position of a portion of the plurality of magnetic dipoles, the changes in position of the portion of the plurality of magnetic dipoles corresponding to a pulse movement of the human skin surface.

18. The pulse sensor of claim 16, wherein the magnet includes a permanent magnet.

19. The pulse sensor of claim 16, wherein the magnet is configured to maintain a substantially constant magnetic field across each of the plurality of magnetic dipoles.

20. The pulse sensor of claim 16, wherein the plurality of magnetic dipoles are configured to magnetically rotate responsive to the periodically reversing magnetic poling field.

21. The pulse sensor of claim 16, wherein the plurality of magnetic dipoles are configured to maintain magnetic polarity in the periodically reversing poling field.

22. The pulse sensor of claim 16, wherein the plurality of magnetic dipoles are held in alignment by a cross-linked component of the flexible substrate.

23. The pulse sensor of claim 22, wherein the alignment of the magnetic dipoles is formed by poling the magnetic dipoles carried by a precursor of the flexible substrate, and cross-linking the cross-linked component to hold the plurality of magnetic dipoles in net magnetic alignment.

24. The pulse sensor of claim 16, wherein the plurality of magnetic dipoles are held in alignment by the flexible substrate.

25. The pulse sensor of claim 16, wherein the magnetic dipoles carry a net magnetic alignment as a group; and wherein individual magnetic dipoles carry respective magnetic axes that differ from the net magnetic alignment.

26. The pulse sensor of claim 16, wherein the magnetic dipoles are aligned along respective radial axes.

27. The pulse sensor of claim 16, wherein the magnetic dipoles are aligned with respective axes that are substantially normal to the flexible substrate.

28. The pulse sensor of claim 16, wherein the magnetic sensor comprises:

a sensor configured to sense a magnetic field along one axis corresponding to the magnetic axis of the magnetic dipoles.

29. The pulse sensor of claim 16, wherein the magnetic sensor comprises:

an X-axis magnetic sensor configured to sense a magnetic field component along an X-axis;

a Y-axis magnetic sensor configured to sense a magnetic field component along a Y-axis; and a Z-axis magnetic sensor configured to sense a magnetic field component along a Z-axis.

30. The pulse sensor of claim 16, wherein the magnetic sensor comprises:

at least one sensor aligned relative to the aligned magnetic dipoles.

31. The pulse sensor of claim 16, wherein the magnetic sensor comprises:

a magnetic sensor array configured to sense magnetic field components at a plurality of locations in a sensor array.

32. The pulse sensor of claim 16, wherein the magnetic sensor is configured to sense one or more magnetic field components less than $10^{-3}$ as strong as the earth's magnetic field.

33. The pulse sensor of claim 16, wherein the magnetic sensor is configured to sense one or more magnetic field components less than $10^{-6}$ as strong as the earth's magnetic field.

34. The pulse sensor of claim 16, wherein the magnetic sensor is arranged as a plurality of sensor modules, each sensor module being configured to sense a magnetic field along a plurality of sensing axes.

35. The pulse sensor of claim 16, further comprising:

a housing configured to carry the flexible substrate, the magnetic sensor, and the analysis circuit, the housing being configured to be worn around a human wrist.

36. The pulse sensor of claim 35, wherein the flexible substrate is elastomeric; and wherein the housing includes a suspension operatively coupled to the flexible substrate, the suspension being configured to urge the flexible substrate against the human skin surface.

37. The pulse sensor of claim 16, further comprising:

an elastomeric foam disposed to press against an outside surface of the flexible substrate, the elastomeric foam being configured to urge the flexible substrate carrying the plurality of magnetic dipoles against the human skin surface.

38. The pulse sensor of claim 16, wherein the magnetic sensor comprises a magnetometer.

* * * * *